United States Patent [19]

Townsend et al.

[11] 4,092,472
[45] May 30, 1978

[54] 2,4-DICHLORO-5-(β-D-RIBOFURANOSYL) PYRIMIDINES AND SUBSTITUTED DERIVATIVES

[75] Inventors: Leroy B. Townsend; Dean Sylvester Wise; Robert Arthur Earl, all of Salt Lake City, Utah

[73] Assignee: University of Utah, Salt Lake City, Utah

[21] Appl. No.: 709,971

[22] Filed: Jul. 30, 1976

[51] Int. Cl.$^2$ .............................................. C07H 3/02
[52] U.S. Cl. ........................................ 536/1; 424/180
[58] Field of Search ...................................... 536/1, 23

[56] References Cited

U.S. PATENT DOCUMENTS 3,998,999  12/1976  DeBernardo et al. .................. 536/1

OTHER PUBLICATIONS

Shapiro et al., Jour. Amer. Chem. Soc., vol. 83, 1961, pp. 3920–3921.

Primary Examiner—Johnnie R. Brown

[57] ABSTRACT

A C-nucleoside compound, 2,4-dichloro-5-(2,3,5-Tri-O-acetyl-β-D-Ribofuranosyl)pyrimidine, useful as a primary starting material in the synthesis of various C-nucleoside compounds having antitumor, antiviral and/or antibacterial activity. A structural formula is as follows:

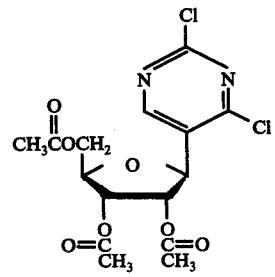

The location of the 2,4-dichloro members on the heterocycle, with the active sites of the carbohydrate being blocked, provides an intermediate compound well adapted for a variety of nucleophilic substitutions. Such procedures have yielded several novel analogs of known pyrimidine nucleosides found in RNA, as well as other compounds which have demonstrated chemotherapeutic utility.

9 Claims, No Drawings

2,4-DICHLORO-5-(β-D-RIBOFURANOSYL) PYRIMIDINES AND SUBSTITUTED DERIVATIVES

Part of the research leading to the invention herein disclosed was funded by grant CI-89 from the American Cancer Society.

Field of the Invention

This invention relates to novel compositions within the set of chemical compounds commonly referred to as C-nucleosides. Specifically, the invention discloses novel compounds of this class derived from the pseudouridine intermediate 2,4-dichloro-5-(2,3,5-Tri-O-acyl-β-D-ribofuranosyl)pyrimidine.

BACKGROUND OF THE INVENTION

The class of compounds referred to as C-nucleosides has captured increased interest due to the effectiveness of many such compounds as antibiotics and potential anti-cancer compositions. The first member of this class to be discovered was pseudouridine, a naturally occurring nucleoside isolated from a variety of t-RNA's. The structure of pseudouridine has been identified as follows:

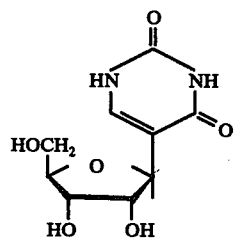

It will be noted that this composition is a union of a heterocyclic moiety, uracil, and a carbohydrate moiety, ribofuranose, in the beta configuration.

Following the isolation of pseudouridine, two new C-nucleosides having strong antibiotic effects were discovered, formycin and formycin B, having the structural formulas illustrated below:

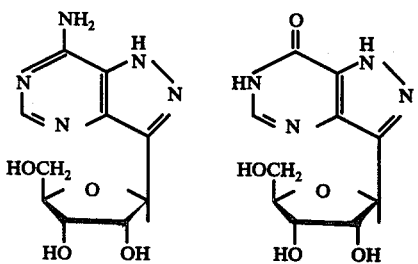

Both compositions have shown additional activity in inhibiting leukemia L-1210, HeLa cells, Ehrlich carcinoma in mice and Yoshida rat sarcoma cells.

Following the isolation of several other C-nucleosides having various levels of antiviral and antitumor activity, a compound identified as oxazinomycin was extracted from the culture filtrate of *Streptomyces tanesashiensis* and from a Streptomyces strain sp. 80,432. Its structure is very similar to pseudouridine, as can be noted below.

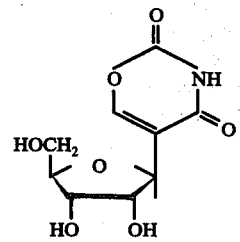

In addition to its anti-bacterial activity, this C-nucleoside exhibits a broad spectrum of antitumor activity, including Ehrlich mouse ascites carcinoma, sarcoma 180 (ascites) and sarcoma 180 (solid form) in vivo.

The antiviral and antitumor effects of the above mentioned compounds, and of the oxazinomycin in particular, suggest the utility of pseudouridine derivatives as potential candidates of similar activity. A primary difficulty in further analysis of pseudouridine was achieving blocked sites on the carbohydrate moiety to permit more detailed study of nucleophilic substitutions of the heterocyclic constituent. In addition, a blocked derivative of pseudouridine was required which could serve as an intermediate, from which various substituted compounds could be prepared.

SUMMARY AND OBJECTIVES

It is therefore a primary objective of this invention to provide a stable derivative of pseudouridine, with the appropriate blocked sites to permit general use as a starting material for various functional group transformations of the heterocyclic moiety.

It is a further object of this invention to provide novel compositions derived from the above stated starting material having antiviral, antibacterial and/or antitumor activity.

The present invention discloses the structural chemical formula and synthesis for a stable derivative of pseudouridine 2,4-dichloro-5-(2,3,5-Tri-O-acetyl-β-D-ribofuranosyl)pyrimidine, having the blocked sites on the carbohydrate moiety required to permit further modification of the functional groups attached to the heterocyclic moiety:

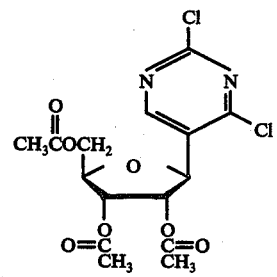

Examples of such derivative compounds include the mono and disubstituted (1) alkylamino, arylamino and amino derivatives, (2) alkylthio and arylthio derivatives, (3) alkoxy and aryloxy derivatives, (4) thione and amino-thione derivatives and (5) selenium derivatives.

DETAILED DESCRIPTION OF THE PREFERRED EMBODIMENTS

This invention relates to the synthesis of 2,4-dichloro-5-(2,3,5-Tri-O-acetyl-β-D-ribofuranosyl)pyrimidine (herein referred to as the "dichloro intermediate") and various compounds derived by nucleophilic substitution on the heterocyclic moiety. The dichloro intermediate has the following specific structural formula wherein the carbohydrate moiety is suitably blocked by acetyl groups, the chlorine being substitutionally representative of the halogen family.

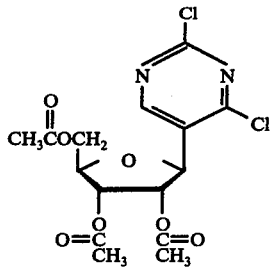

Other members of the acyl group having the generic formula RCO— are likewise used as blocking members and provide the protection against reactions intended for nucleophilic substitution at the heterocyclic ring only. Although most acyl groups are susceptible to incorporation at the blocking sites, the acetyl, benzoyl, p-nitrobenzoyl and chloroacetyl are among the more commonly used. A more general structural formula reflecting the variation of blocking members on the carbohydrate moiety is provided, to wit:

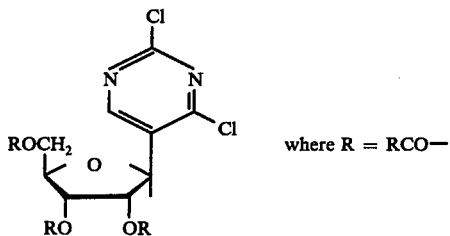

wherein RCO— represents any member of the acyl group as represented by the abovenamed lower acyl members. The blocked carbohydrate moiety shall hereinafter be referred to in chemical formula as 2,3,5-Tri-O-acyl-β-D-ribofuranosyl, which is to be interpreted to include the alternative variations among members of the acyl group as previously explained.

The dichloro intermediate is a valuable tool in C-nucleoside research because it provides a means to synthesize many new compounds within this class by substitution from a preformed nucleoside rather than requiring construction of a new molecule from smaller parts. Currently, the synthesis of derivatives of pseudouridine involves long and arduous procedures with low yields and high costs being among the primary results. Furthermore, the construction of these C-nucleosides from segments of the final product usually results in an end product which is a combination of several different compounds including both alpha and beta anomers of the carbohydrate.

For applications involving human metabolic studies, the beta configuration is required to comport with naturally occurring beta nucleosides. By starting with the dichloro intermediate in the beta orientation, substitutions are made on the respective moieties yielding the desired beta nucleoside without concurrent anomerization. Furthermore, the dichloro intermediate has important utility as a starting material because it yields C-glycoside end products which are not catabolized by phosphorylase as are N-glycosides. Such compounds can therefore be more easily transported through cell membrane for potential antimetabolite activity.

In addition to the important beta orientation and C-glycoside structure, the dichloro intermediate is suitably blocked to protect the carbohydrate moiety from concurrent undesirable reactions, thereby permitting the highly electrophilic chlorine atoms on the heterocycle to be subjected to a broad spectrum of nucleophilic substitutions without damaging the C-nucleoside or its carbohydrate moiety. The amenability of this dichloro intermediate to nucleophilic substitution provides greatly increased yields and purity of end product, a significant advance over the prior art relating to the preparation of C-nucleosides.

SYNTHESIS OF THE DICHLORO INTERMEDIATE

Treatment of any 2',3',5'-Tri-O-acyl-pseudouridine with phosphoryl chloride, with or without a catalyst such as diethylaniline hydrochloride, yields 2,4-dichloro-5-(2,3,5-Tri-O-acyl-β-D-ribofuranosyl)pyrimidine, the dichloro intermediate. Preparation of Tri-O-acyl pseudouridine may be by any of numerous current methods of acylation, including that disclosed in Bobek, Farkas and Sorm, *Coll. Czeck. Chem. Comm.* 341:1690 (1969) involving the reaction of acetic anyhydride and pyridine or benzoyl chloride and pyridine. Reaction conditions for the chlorination of 2',3',5'-Tri-O acylpseudouridine are not critical; however, variations will result in different % yields and variable degrees of purity. A suggested set of reaction conditions are set forth in the following reaction scheme.

5-(2,3,5-Tri-O-acetyl-β-D-ribofuranosyl) uracil (5g, 13.5 mmol) and diethylaniline hydrochloride (2.5g, 13.5 mmol) were dried separately for three hours at 50° C and 0.1 mm Hg. It is important to note that other catalysts can be substituted for the diethylaniline hydrochloride, including other salts of tertiary amines such as pyridine hydrochloride and dimethylaniline hydrochloride. The effect of the catalyst is to increase the chloride ion concentration and thereby drive the reaction forward. Therefore, any chloride salt which is nonreactive with other solution constituents would catalyze the reaction. The phosphoryl chloride itself will sustain a chlorination reaction, but yields will be at lower levels.

These reactants were combined and added to an excess of phosphoryl chloride (50 ml). The mixture was then heated at reflux temperature for 2½ hours. The reaction temperature may be varied from ambient to reflux; however, the best yields occur at reflux. The reaction mixture was then concentrated to 5 ml under reduced pressure and poured over crushed ice (15 g) and then diluted with 200 ml of ice-water. This solution was extracted with diethyl ether (400 ml, 100 ml × 2). The ether extracts were combined and washed successively with cold water (200 ml), cold saturated aq. NaHCO₃ (50 ml), and then cold saturated aq. NaCl solution (25 ml). The ether layer was dried over anhydrous Na₂SO₄ (about 8 hours) filtered to remove the drying agent and concentrated in vacuo to obtain a colorless solid. This solid material was collected by filtration and recrystallized from diisopropyl ether to yield 4.14 g (75.3%) of 2,4-dichloro-5-(2,3,5-Tri-O-acetyl-β-D-ribofuranosyl)pyrimidine. Physical characteristics for the compound are as follows: m.p. 75°–78°;

$[\alpha]_D^{27°} = +24.6°$, c = 12 mg/ml, DMF; uv, $\lambda_{max}^{EtOH}$ 264 nm, pmr (CDCl$_3$) 8.89 δ (Aromatic).

Anal. Calcd. for $C_{15}H_{16}Cl_2N_2O_7$: C, 44.24; H, 3.96; N, 6.88. Found: C, 44.38; H, 4.08; N, 6.95.

The dichloro acetyl intermediate possesses excellent stability under normal laboratory conditions.

DERIVATIVES OF THE DICHLORO-INTERMEDIATE

With the carbohydrate moiety appropriately blocked, the heterocyclic moiety can be subjected to nucleophilic substitution at the chlorine locations. The procedures for such reactions are well known in the art, particularly where the substitution is for a chlorine as in the present case. The following are examples of general classes of derivatives available from the dichloro intermediate.

EXAMPLE 1

Alkyloxy/Aryloxy Derivatives

The reaction of the dichloro intermediate with equimolar amounts of an alcoholate yields the corresponding alkoxy or aryloxy substituted derivatives having the chemical formula 4-alkoxy(or aryloxy)-2-chloro-5-(β-D-ribofuranosyl)pyrimidine or the corresponding isomers 2-alkoxy(or aryloxy)-4-chloro-5-(β-D-ribofuranosyl)pyrimidines. Reaction of one molar equivalent of the dichloro intermediate with 2 molar equivalents or more of an alcoholate will provide the 2,4-disubstituted alkoxy (or aryloxy)-5-(β-D-ribofuranosyl)pyrimidines.

A dimethoxy derivative of the dichloro intermediate has been prepared, being a lower alkoxy member, representative of the general alkyloxy and aryloxy derivatives having a structural formula as follows:

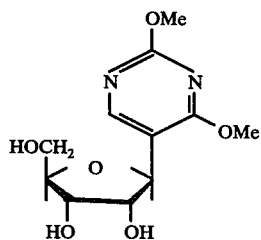

and is also known by the chemical name 2,4-dimethoxy-5-(β-D-ribofuranosyl)pyrimidine. This compound is prepared from the reaction of one molar equivalent of 2,4-dichloro-5-(2,3,5-Tri-O-acetyl-β-D-ribofuranosyl)-pyrimidine with greater than 2 molar equivalents of sodium methylate in accordance with commonly known reaction procedures. The acyl blocking groups are concurrently removed by the basic effect of the sodium methylate. An illustration of a specific method of preparation follows.

Sodium metal (0.14 g, 10 mmole) was added to 20 ml of absolute methanol and the mixture stirred until homogeneous. To this solution was added 2,4-dichloro-5-(Tri-O-acetyl-β-D-ribofuranosyl)pyrimidine (0.814 g., 2 mmole) and the resulting mixture was heated at reflux for 3 hours. The solution was cooled to room temperature and then neutralized with dry ice. The solvent was removed under reduced pressure and the resulting syrup applied to a chromatography column (SilicAR CC-7, 3.5 × 10 cm) and eluted with a chloroform: methanol (9:1 by volume) mixture. The fractions which contained the product were combined and evaporated under reduced pressure to a white foam which was recrystallized from water, to yield 385 mg (71%) of 2,4-Dimethoxy-5-(β-D-ribofuranosyl)pyrimidine, m.p. 138°–139°, pmr DMSO-d$_6$: δ 4.03 (6H, S, OCH$_3$); δ 4.90 (1H, d, H$_1$'); δ 8.67 (1H, S, C$_6$.H) uv $\lambda_{max}^{pH\,7}$ 264. Mass spectrum M$^+$ 272 + 3TMS.

In vitro testing of the dimethoxy derivative at the University of Utah has clearly indicated inhibition of leukemia L 1210 at a concentration of 10$^{-4}$ Molar. The additional fact that this C-glycoside should not be a substrate for phosphorylase strengthens the utility of this antimetabolite for possible chemotherapeutic purposes. The commonality between the structure and chemical characteristics of the dimethoxy derivative with the other derivatives outlined in this class suggests broad utility for chemotherapeutic activity among substantially all the alkoxy and aryloxy derivatives. Further support of this proposition is found in *J. of Medicinal Chemistry*, 18, 5:473–475, (1975), which points out the activity of 4-(β-D-Ribofuranosyl)-1,3-dibenzyloxybenzene against leukemia L 1210 at 7 × 10$^{-6}$ Molar.

EXAMPLE 2

Amino, Arylamino and Alkylamino Derivatives

The reaction of the dichloro intermediate with equimolar amounts of alkylamines, arylamines or ammonia yields the corresponding alkylamino, arylamino or amino substituted derivatives having the chemical formula 4-alkylamino (arylamino or amino)-2 chloro-5-(β-D-ribofuranosyl)pyrimidine or the isomer 2-alkylamino (arylamino or amino)-4-chloro-5-(β-D-ribofuranosyl)-pyrimidine. Reaction of one molar equivalent of the dichloro intermediate with 2 molar equivalents or more of alkylamines, arylamines or ammonia will provide the 2,4-disubstituted alkylamino (arylamino or amino)-5-(β-D-ribofuranosyl)pyrimidines.

The 2-amino-5-(β-D-ribofuranosyl)pyrimidin-4-one (also known as pseudo-isocytidine) has been successfully prepared by other procedures and has been introduced into preclinical studies for pharmocological and toxicological testing. This compound has shown excellent activity against acute myeloblastic leukemia, as well as inhibition of other leukemic cells as discussed in Burchenal, et. al., Antileukemic Effects of Pseudoisocytidine, a New Synthetic Pyrimidine C-Nucleoside, Cancer Research, 36, 1520–1523, April 1976. The close similarity of this compound with the other members of the amino, alkylamino and arylamino class of derivatives is a strong indication of the potential usefulness of this class of compounds as anticancer agents.

The following method for preparation of the 2-amino -5-(β-D-ribofuranosyl)pyrimidin-4-one is illustrative for other members of this class. 2-Amino-4-chloro-5-(β-D-ribofuranosyl)pyrimidine (262 mg, 1 mmole) was added to 10 ml of water containing sodium acetate (820 mg 10 mmole) and heated at reflux for 3 hours. The solvent was removed under reduced pressure and the residue dissolved in MeOH and absorbed onto 2g of SilicAR CC-7. This solid was then applied to the top of a 2.5 × 10 cm column of SilicAR CC-7 and eluted with chloroform: methanol (4:1 by volume). The fractions containing the product were combined and evaporated to a white residue which was recrystallized from a 10% methanolic HCl to afford 225 mg (81%) of 2-Amino-5-(β-D-ribofuranosyl)pyrimidin-4-one, mp. 216°–217°. This product was identical in all physical respects to that reported in the literature. *J. Heterocyclic Chem.*, 12, 817 (1975).

Because of the favorable results of the previous amine, 2-Amino-4-chloro-5-(β-D-ribofuranosyl)pyrimidine and 4-Amino-2-chloro-5-(β-D-ribofuranosyl)-pyrimidine have also been prepared, with a similar antimetabolic character predicted, due in part to the common functional amino. The detailed method of preparation for these isomers is as follows, respectively.

2,4-Dichloropyrimidine (1.76 g, 4.3 mmole) was suspended in 10 ml of liquid ammonia in a sealed stainless steel reaction vessel and allowed to stand at 27° C for 24 hours. The ammonia was allowed to evaporate to leave a light brown syrup. The syrup was treated with 5 ml of ethyl acetate and 5 ml of isopropanol to produce a semicrystalline solid. This material was removed by filtration and recrystallized from water to yield 0.5 g (44%) of 2-amino-4-chloro-5-(β-D-ribofuranosyl)pyrimidine, mp. 195°–197° C, m.p. 195°–197° C, uv $\lambda_{max}^{pH\ 1}$ 230, 311 nm; $\lambda_{max}^{pH\ 11}$ 236,302 nm; $\lambda_{max}^{MeOH}$ 237, 303; pmr (DMSO-d$_6$): δ 8.42 (s, 1H, H-6); δ 6.9–6.95 (s, 2H, NH$_2$); δ 4.78 (d, J = 3.6 Hz, 1H, anomeric proton). Mass spectrum M+ 262 + 4 TMS.

The filtrate from above was evaporated to a syrup and applied to a chromatography column (SilicAR CC-7, 3.5 × 20 cm) and eluted with chloroform-methanol(9:1 by volume), 10 ml fractions being collected. Fractions which contained a product with an Rf of 0.65 (tlc, SilicAR 7 GF CHCl$_3$/MeOH, 10:1 by volume) were combined and the solvent removed under reduced pressure to yield a colorless powder which was recrystallized from isopropanol to yield 0.35g. (31%) of 4-amino-2-chloro-5-(β-D-ribofuranosyl)pyrimidine, m.p. 98°–99°, uv $\lambda_{max}^{pH\ 1}$ 252 nm $\lambda_{max}^{pH\ 11}$ 238,277 nm $\lambda_{max}^{MeOH}$ 240,276 nm; pmr (DMSO-d$_6$): δ 8.00 (s, 1H, H-6); δ 7.42 (s, 2H, NH$_2$); δ 4.55 (d, J = 4.5, 1H, anomeric proton); mass spectrum M+ 262 + 4 TMS.

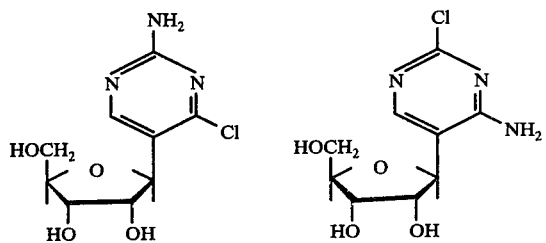

EXAMPLE 3

Alkylthio and Arylthio Derivatives

The reaction of the dichloro intermediate with equimolar amounts of alkylthiolates or arylthiolates yields the corresponding alkylthio or arylthio substituted derivatives having the chemical formula 4-alkylthio (or arylthio)-2-chloro-5-(β-D-ribofuranosyl)pyrimidine or the corresponding isomers 2-alkylthio (or arylthio)-4 chloro-5-(β-D-ribofuranosyl)pyrimidine. Reaction of one molar equivalent of the dichloro intermediate with two molar equivalents or more of alkylthiolates or arylthiolates will provide the 2,4-disubstituted alkylthio (or arylthio)-5-(β-D-ribofuranosyl)pyrimidines. It is expected from the common family membership on the periodic table that the alkylthio will be of similar or greater activity to the alkyloxy group. In most cases the displacement of the oxygen by a sulfur has increased antimetabolite activity of the nucleoside.

EXAMPLE 4

Thione and Amino-Thione Derivatives

The reaction of one molar equivalent of the dichloro intermediate in basic solution with two molar equivalents of hydrogen sulfide salts or thiourea yields 5-(β-D-ribofuranosyl)pyrimidin-2,4-dithione, having the following structural formula:

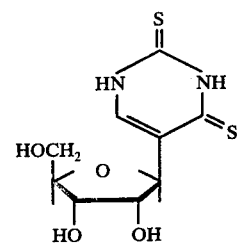

Further reaction of the dithione derivative with ammonia, alkylamines or arylamines provides 4-amino (alkylamino or arylamino)-5-(β-D-ribofuranosyl)-pyrimidin-2-thione.

The 5-(β-D-ribofuranosyl)pyrimidin-4-thione-2-one (also known as 4-thio-pseudouridine) is a well known member of the thione class of derivatives and has been shown to have significant antibacterial activity. Wigler, et al, Effects of 4-Thiopseudouridine on the Salvage of Pseudouridine by Excheriehia Coli Cells, *J. of Carbohydrates, Nucleosides and Nucleotides* 1, 4:307–321, (1974), discusses previous methods of preparation and findings as to antibacteriological effects. The closeness of character between oxygen and sulfur and the tendency of sulfur to increase activity of the heterocycle suggests the value of the several derivatives associated in this class.

EXAMPLE 5

Selenium Derivatives

Similar to the derivatives of oxygen and sulfur, the selenium nucleophile should have potential antitumor activity and can be substituted as alkyl and aryl seleno, selone and similar selenium derived compositions at both the 2 and 4 heterocyclic positions.

GENERAL METHOD OF PREPARATION OF PSEUDOURIDINE DERIVATIVES

Using pseudouridine as the starting material, a broad spectrum of nucleophilic substitutions can be accomplished by utilizing the following procedures:

1. Preparation of the 2′, 3′,5-Tri-O-acyl-pseudouridine using current methods of acylation.
2. Synthesis of the 2,4-dichloro-5-(2,3,5-Tri-O-acyl-β-D-ribofuranosyl)pyrimidines by procedures outlined supra.
3. Nucleophilic substitution of the heterocycle in accordance with current procedures, as suggested in each of the previous examples enumerated.

Utilizing this general method of preparation, the derivatives of the dichloro intermediate can be categorized into four basic structural formulae.

STRUCTURE I

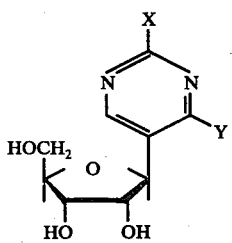

In this aromatic configuration the possible nucleophilic substitutions derived from the dichloro intermediate include compositions defined by the structure above in which X and Y respectively are selected from any of the following (herein designated as Group I) in any combination:

GROUP I

Amino, alkylamines, and aryl amines
Chloride, bromide, iodide, fluoride
Alkoxy, aryloxy, akylseleno, aryl seleno
Alkylthio, arylthio

STRUCTURE II

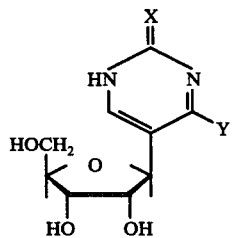

The variations of nucleophilic substitutions in the above structure include compositions defined structurally herein where Y is selected from any member of Group I, and X is selected from either oxygen, sulfur, and selenium, including combinations thereof.

STRUCTURE III

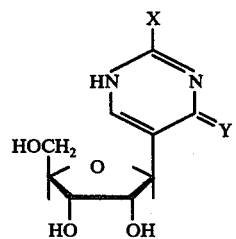

This structure is the isomer of structure II, with X being selected from any of Group I and Y being selected from oxygen, selenium and sulfur, and including all combinations thereof.

STRUCTURE IV

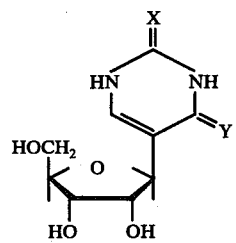

The three variations within this structure include derivatives defined by the indicated structure in which X is sulfur and Y is either oxygen, sulfur or of selenium.

Of the compositions comprised by the four structures illustrated, three compounds have been formerly prepared, as has been previously mentioned. These compounds are the 4-thiopseudouridine (X=O, Y=S in Structure IV), 2-amino-4-oxo-5-($\beta$-D-ribofuranosyl)-pyrimidine and its isomer, 4-amino-2-oxo-5-($\beta$-D-ribofuranosyl)pyrimidine (enumerated in Structures III and II respectively).

Although, discussion of nucleophilic substitution has centered around the use of the dichloro intermediate, other members of the halogen family could likewise be used as the locations for substitution. Chlorine was selected as the primary example due to its aminable nature with respect to nucleophilic substitution. To conform the respective portions of the disclosure to bromine, iodine or fluorine, the appropriate halogen should simply be substituted for the chlorine atom, with the usual reaction modifications which may be required. The additional intermediates 2,4-dibromo-5-(2,3,5-Tri-O-acyl-$\beta$-D-ribofuranosyl)-pyrimidine
2,4-diiodo-5-(2,3,5-Tri-O-acyl-$\beta$-D-ribofuranosyl)-pyrimidine
2,4-difluoro-5-(2,3,5-Tri-O-acyl-$\beta$-D-ribofuranosyl)-pyrimidine are therefore comprehended within the scope of this disclosure.

We claim:

1. A compound, 2,4-dihalo-5-(2,3,5-Tri-O-acyl-$\beta$-D-ribofuranosyl)pyrimidine, having the structural formula

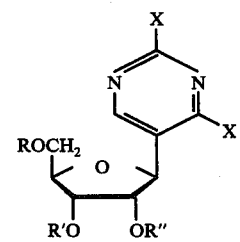

wherein R, R' and R" respectively are selected from a lower acyl organic group and X is selected from the group consisting of chlorine, bromine, iodine and fluorine.

2. The compound as defined in claim 1, wherein R is acetyl, said compound, 2,4-dihalo-5-(2,3,5-Tri-O-acetyl-$\beta$-D-ribofuranosyl)pyrimidine, having the structural formula:

3. A compound, 2,4-dichloro-5-(2,3,5-Tri-O-acetyl-β-D-ribofuranosyl)pyrimidine, pyrimidine, having the structural formula:

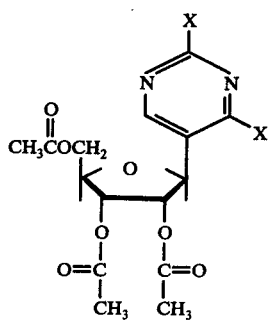

4. A compound of the formula

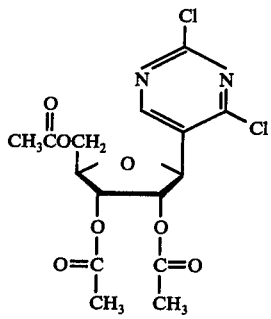

wherein X is selected from the group consisting of
Amino, lower alkylamine, lower aryl amine
Chloride, bromide, iodide, fluoride
Lower Alkoxy, lower aryloxy, lower akylseleno, lower aryl seleno
Lower Alkylthio, and lower arylthio;
and Y is selected from the group consisting of
Amino, lower alkylamine, lower aryl amine
Chloride, bromide, iodide, fluoride
Lower Alkoxy, lower aryloxy, lower akylseleno, lower aryl seleno
Lower Alkylthio, and lower arylthio.

5. A compound as defined in claim 4, 2-amino-4-chloro-5-(β-D-ribofuranosyl)pyrimidine, having the structural formula

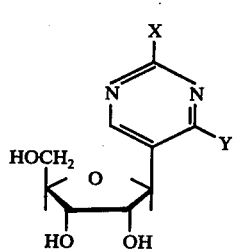

6. A compound as defined in claim 4, 4-amino-2-chloro-5-(β-D-ribofuranosyl)pyrimidine, having the structural formula

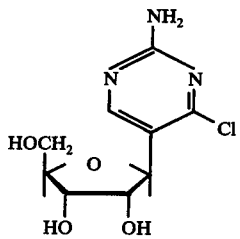

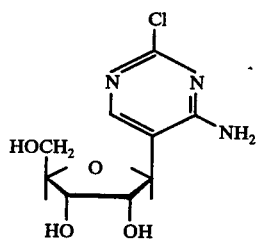

7. A compound of the formula

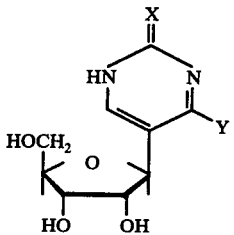

wherein X is selected from the group consisting of oxygen, sulfur and selenium and Y is selected from the group consisting of
Amino, lower alkylamine, lower aryl amine
Chloride, bromide, iodide, fluoride
Lower Alkoxy, lower aryloxy, lower akylseleno, lower aryl seleno
Lower Alkylthio, and lower arylthio;
excluding the compound 4-amino-2-oxo-5-(β-D-ribofuranosyl)pyrimidine.

8. A compound of the formula

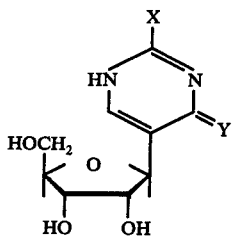

wherein Y is selected from the group consisting of sulfur, selenium and oxygen and X is selected from the group consisting of
Amino, lower alkylamine, lower aryl amine
Chloride, bromide, iodide, fluoride
Lower Alkoxy, lower aryloxy, lower akylseleno, lower aryl seleno
Lower Alkylthio, and lower arylthio;

excluding the compound 2-amino-4-oxo-5-(β-D-ribofuranosyl)pyrimidine.
9. A compound of the formula
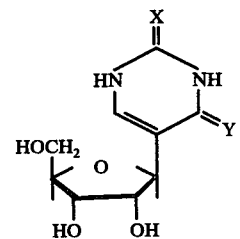
wherein X is selected from the group consisting of sulfur and selenium and Y is selected from the group consisting of selenium, oxygen and sulfur.
* * * * *